United States Patent [19]

Shapiro

[11] Patent Number: 4,573,778

[45] Date of Patent: Mar. 4, 1986

[54] AQUEOUS FLUOROPHOTOMETER

[75] Inventor: Jerrold M. Shapiro, Framingham, Mass.

[73] Assignee: Boston University, Boston, Mass.

[21] Appl. No.: 475,854

[22] Filed: Mar. 16, 1983

[51] Int. Cl.⁴ .............................................. A61B 3/00
[52] U.S. Cl. ................................... 351/219; 351/221; 351/160 H
[58] Field of Search .............. 351/205, 219, 221, 220, 351/160 R, 160 H

[56] References Cited

U.S. PATENT DOCUMENTS 3,820,879  6/1974  Frisen .................................. 351/219
4,134,647  1/1979  Ramos-Caldera .................. 351/219

OTHER PUBLICATIONS

Furukawa et al., "Slit Lamp Fluorophotometry", Optical Engineering vol. 15, No. 4, pp. 321-324, Jul.-Aug. 1976.

Primary Examiner—Rodney B. Bovernick
Assistant Examiner—P. M. Dzierzynski

[57] ABSTRACT

Fluorescence of the anterior chamber of an eye is determined by projecting a ribbon of light from the side of the eye through the anterior chamber in a direction generally perpendicular to the optic axis of the eye. The ribbon of light is obtained by imaging the face (20) of a fiber optic bundle (18) and directing that image into the anterior chamber by a mirror (30) mounted adjacent to a contact lens (40). The contact lens (40) includes a flexible membrane (14) backed by a fluid. The pressure of the fluid can be varied by a syringe (44) to vary the curvature of the contact lens membrane (14). The fluorescence can be detected either directly by a photodiode (68) or through a fiber optic bundle (34) by a photomultiplier (76).

14 Claims, 5 Drawing Figures

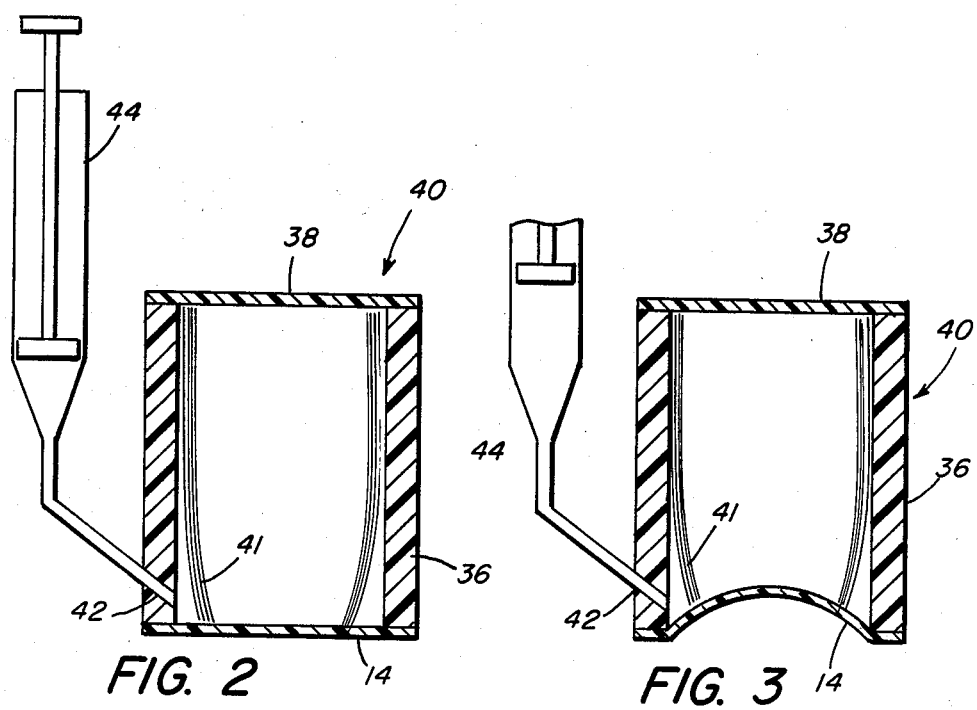
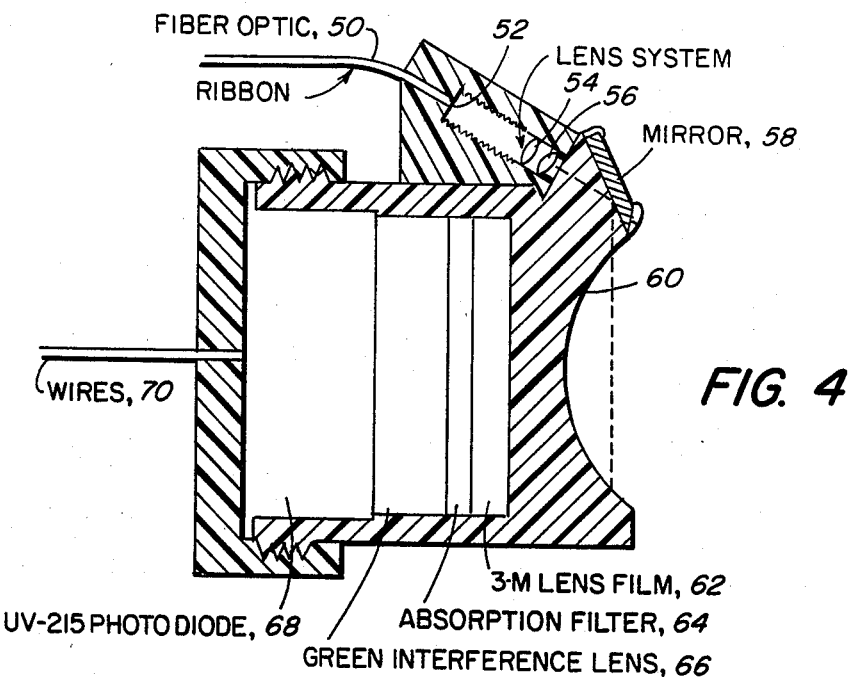

AQUEOUS FLUOROPHOTOMETER

TECHNICAL FIELD

This invention relates to ophthalmological devices and in particular to devices for detecting the fluorescence of the aqueous humor in the anterior chamber of the eye.

BACKGROUND

For testing and diagnostic purposes, it is at times useful to determine the fluorescence of the aqueous humor which is in the anterior chamber between the cornea and the lens of the eye. For example, such a determination can be used to test the effectiveness of anti-glaucoma therapeutics, to test the bioavailability of drugs and to test for the inflammatory response.

The shape of the normal eye is maintained by an internal fluid pressure of about 15 millimeters of mercury. That intraocular pressure (IOP) is controlled by the balance of flow of aqueous humor due to secretion from and filtration through the ciliary body and drainage through the trabecular meshwork. In the disease of glaucoma, the balance is disturbed. The result is an increase in IOP which eventually damages the optic nerve and causes blindness.

Aqueous humor is a watery fluid produced by the ciliary body in the posterior chamber behind the iris. Aqueous humor then flows through the pupil and the anterior chamber and drains through the trabecular meshwork. The IOP increases when the resistance to flow through the trabecular meshwork is great relative to the amount of aqueous humor which is produced. Some drugs used to treat glaucoma reduce the rate of formation of aqueous humor.

Aqueous fluorophotometry is a method used to observe the flow rate of aqueous humor through the anterior chamber of the eye. Such observations are important in understanding the pathophysiology of glaucoma and the mechanics underlying the effects of antiglaucomatous drugs. According to this method, a fluorescent dye is instilled into the anterior chamber. This may be accomplished by placing a drop of aqueous dye on the cornea; the fluorescent dye passes through the cornea into the anterior chamber. The changing concentration of the fluorescent dye in the anterior chamber is directly related to the flow rate of aqueous humor. The concentration of the dye has in the past been determined by projecting light into the anterior chamber using a slit lamp and detecting the resultant corneal and aqueous fluorescence. In such systems, only about one part in a billion of the light leaving the projection lamp is detected. Accordingly, expensive photomultiplier light measurement systems have been used and the systems have suffered fairly large measurement errors. Further, where the dye is instilled into the anterior chamber through the blood, the iris behind the anterior chamber can be fluorescent, and that fluorescence can interfere with the measurements.

In addition to testing for the flow of aqueous humor, aqueous fluorophotometry can be used to judge the bioavailability of drugs and the inflammatory response. The bioavailability of a drug is the ability of that drug to penetrate into the eye. By placing a fluorescent tag on the drug and applying it to the eye, the aqueous fluorescence is an indication of the degree of penetration of the drug into the anterior chamber.

During the inflammatory response of a body, large fluorescent molecules injected into the blood are more likely to penetrate the walls of the blood vessels and enter the anterior chamber. A large amount of fluorescent molecules in the anterior chamber indicates a significant inflammatory response which in turns indicates a significant inflammation. A test for aqueous fluorescence can be used diagnostically to determine whether there is an inflammation and therapeutically to determine the response of the body to treatment. In the past, the inflammatory response has been measured by observing the scattering of light by white blood cells and large protein molecules which pass from the blood vessels into the anterior chamber. A more efficient aqueous fluorophotometry test will provide a quantitative and objective test which has not heretofore been available.

DISCLOSURE OF THE INVENTION

The aqueous fluorescence can be measured by transmitting a beam of light across the anterior chamber and detecting the resultant fluorescent light from the front of the eye. To enable the projection of light across the anterior chamber without having that light refracted toward the eye's lens by the cornea, a contact lens is positioned against the cornea. Preferably, the contact lens has a mirror for reflecting light received from a direction in front of the eye to a direction across the anterior chamber generally perpendicular to the optic axis. Fluorescent light can be detected by a photodetector mounted directly to the contact lens, or the light can be transmitted through fiber optics to a separate detector.

To allow for movement of the eye, the light projected into the eye is projected through a fiber optic bundle, one end of which is fixed relative to the contact lens mirror. A rectangular fiber optic face is projected as a ribbon of light across the anterior chamber.

So that the device can be used on eyes having a wide range of corneal curvatures, a flexible contact lens membrane is utilized. The contact lens membrane is backed by a fluid which has an index of refraction near to that of the lens and of the cornea in order to minimize refraction of the light toward the eye's lens. The pressure of that fluid can be adjusted to adjust the curvature of the contact lens membrane.

The flexible contact lens membrane spans one end of a barrel which contains the fluid. A flexible light stop in the barrel presses against the flexible contact lens membrane to prevent light scattered by the contact lens membrane from reaching the photodetector. As the flexible contact lens membrane is drawn into the barrel, it causes additional flexure of the light stop.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is an enlarged illustration of the lens barrel in the device of FIG. 1 with the fluid pressure behind the lens equal to ambient pressure;

FIG. 3 is a view similar to FIG. 2 but illustrating the effect of a reduced pressure in the fluid chamber on the curvature of the lens;

FIG. 4 is a cross sectional view illustrating an alternative embodiment of the invention utilizing a fixed curvature lens and a photodiode mounted to the lens;

DESCRIPTION OF A PREFERRED EMBODIMENTS

Figure 1:
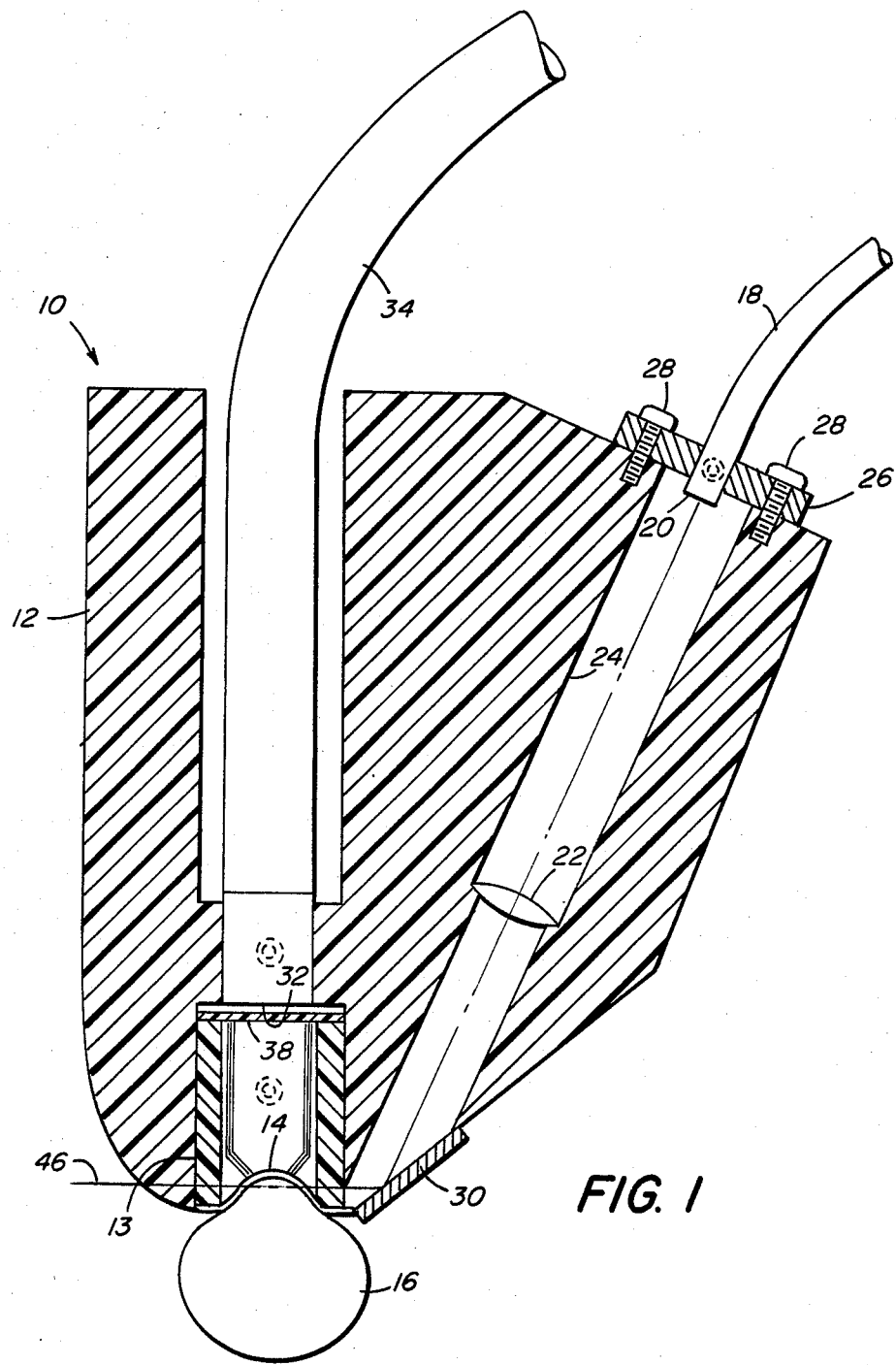
FIG. 1 is a cross sectional view of a preferred embodiment of the invention.

FIG. 1 is a cross sectional view of a preferred contact lens assembly 10 for illuminating the anterior chamber of the eye with a ribbon of light from the side of the eye and for detecting fluorescent light from the front of the eye. A plastic housing 12 is of a size to be held by hand to position a contact lens membrane 14 against the cornea of an eye 16. A first fiber optic bundle 18 serves as a source of blue excitation light. The bundle has a rectangular end face 20 positioned at the end of a bore 24 and is imaged by a lens 22 into the eye. The cable 18 is fixed to a plate 26 which is held by screws 28 to the housing 12. The screws 28 pass through slots in the plate 26 so that the position of the plate 26 can be adjusted to center the end face 20 on the optic axis of the device.

The light focused by the lens 22 is reflected by a mirror 30 to a direction generally perpendicular to the optic axis of the eye 16. The image of the end face 20 is focused at about the optic axis of the eye in the anterior chamber. As a result, the beam of light through the anterior chamber is a ribbon about 7 millimeters wide and 1 millimeter thick at the focal point. The ribbon of light traverses approximately 8 millimeters across the anterior chamber. The blue excitation light causes the dye in the anterior chamber to fluoresce green. The fluorescent light which radiates outwardly through the front of the cornea is picked up at the end face 32 of a second fiber optic bundle 4. The fiber optic bundle 34 carries the light back to a photodetector for subsequent processing.

The contact lens membrane 14 is mounted to a cylinder 36 shown in greater detail in FIG. 2. The cylinder 36 is positioned in an end bore in the housing 12 and fixed thereto by a set screw through the housing. The cylinder 36 is of rigid plastic material closed at the rear end by a transparent window 38. The front end is closed by a flexible, water impermeable membrane 14. Items 14, 36, 38, 44 and 41 comprise the contact lens 40. A cylinder 41 of black, flexible, flock paper is positioned within the cylinder 36 with one end flexed and resting against the membrane 14. The cylinder is filled with a transparent, nonfluorescent fluid. Excitation light from the mirror 30 passes through the cylinder, fluid and contact lens membrane to the eye.

The fluid pressure within the contact lens 40 can be controlled through a port 42 (on FIG. 2) which leads to a syringe 44. The syringe is mounted to the near or far side of the device as shown in FIG. 1 and is thus not itself shown in FIG. 1. By pulling the plunger of the syringe outward as shown in FIG. 3, the pessure in the cylinder 36 can be reduced relative to ambient pressure, and the contact lens membrane 14 is thereby drawn into the chamber. The extent to which the syringe plunger is withdrawn determines the curvature of the contact lens membrane 14. The syringe can thus be calibrated so that the contact lens membrane 14 can be readily set to match the curvature of an eye. Due to the wide variation in corneal curvature among subjects in a given test, and due to the necessity for a close fit of the contact lens membrane to the cornea, it is essential that the curvature of the contact lens membrane can be easily and quickly varied.

It is important that the curvature of the contact lens membrane 14 be established by the internal pressure of the chamber rather than by pressing the flexible lens directly against the eye. If the flexible membrane were simply pressed against the eye, pressure would be applied to the eye and the flow of aqueous humor through the trabecular network would be increased, thereby disturbing the results of the measurement of the rate of flow of aqueous humor.

When a series of tests of an animal or patient are to be made, the curvature need only be determined prior to the first test. Thereafter, the curvature can be quickly set according to the syringe calibration. In making a test, the curvature of the lens is set and the lens is held against the eye for five to 10 seconds while a reading is made. The lens can then be removed and the curvature can be reset for the next test animal. Such a test must be made for each animal at least three times over a period of about three hours to determine the flow of aqueous humor. The adjustable curvature of the lens is particularly important where testing of as many as hundreds of animals must be made in a limited period of time. It would not be feasible to select a separate fixed cuvature lens for each test.

As the contact lens membrane 14 is drawn into the cylinder 36, it presses back against the flexible flock paper 41. The flock paper thus rests against the lens at all curvatures. The paper serves as a light stop to prevent any light reflected by the lens from reaching the detector bundle end face 32.

The flock paper provides an aperture of about 6 millimeters diameter for detecting fluorescence caused by the 7 millimeter wide and 1 millimeter deep ribbon of light. The wide ribbon of light across the anterior chamber illuminates ten thousand times the detectable volume of aqueous humor as would a slit lamp. With a slit lamp, where the beam is directed toward the lens, only a small segment of the excited fluorescence can be detected to avoid detecting fluorescence from the lens and iris.

The contact lens membrane 14 has an index of refraction of 1.49 and the water which serves as the fluid behind the lens has an index of refraction of 1.33. Because both the plastic contact lens membrane 14 and the fluid behind the membrane have indices of refraction substantially matching that of the cornea, about 1.38, there is little refraction of the illuminating beam of light at the cornea. Without this arrangement, the beam of blue excitation light would not continue along the axis 46 across the anterior chamber but would be refracted and redirected toward the iris or lens of the eye. The detected fluorescence would then include the fluorescence of the iris and lens. The detected fluorescence would not provide a true measurement of the fluorescence of the aqueous humor.

The plastic material which has been found most suitable for the membrane 14 is polyvinyl chloride (PVC). The PVC is clear and flexible and has an index of refraction of 1.49. Further, it is impermeable to water and to the dye-containing aqueous solution which is applied to the eye.

FIG. 4 is a cross sectional view of another embodiment of the contact lens assembly. Although this embodiment embodies certain principles of the invention, it has been found less suitable than that of FIG. 1 because it utilizes a fixed cuvature contact lens. Further, the photodetector is mounted directly to the lens and the transmission of an electrical signal from the photodetector to an amplifier results in greater electrical noise than the transmission of light by a fiber optic bundle to an electrically shielded detector and closely associated amplifier.

The embodiment of FIG. 4 includes a fiber optic ribbon light source 50 much like that in the first embodiment. The image of the end face 52 of the fiber optics is focused by lenses 54 and 56 and reflected by a mirror 58. The mirror 58 directs the ribbon of light through the fixed curvature lens element 60 and across the anterior chamber.

The fluorescent light from the anterior chamber passes outward through the lens 60 and a lens film 62. The lens film serves to pass rays of light which are perpendicular to its surface, and to block nonperpendicular rays of light, such as those reflected by the surface of the lens 60. The fluorescent light then passes through an absorption filter 63 which serves to absorb blue illuminating light which may have been reflected outward from the anterior chamber. Finally, the light passes through a green interference filter 66 which passes only the green fluorescent light. The light which psses through the filters is detected by photodiode 68 mounted on the contact lens assembly. The photodiode output is passed on a lead 70 to processing electronics.

Figure 5:
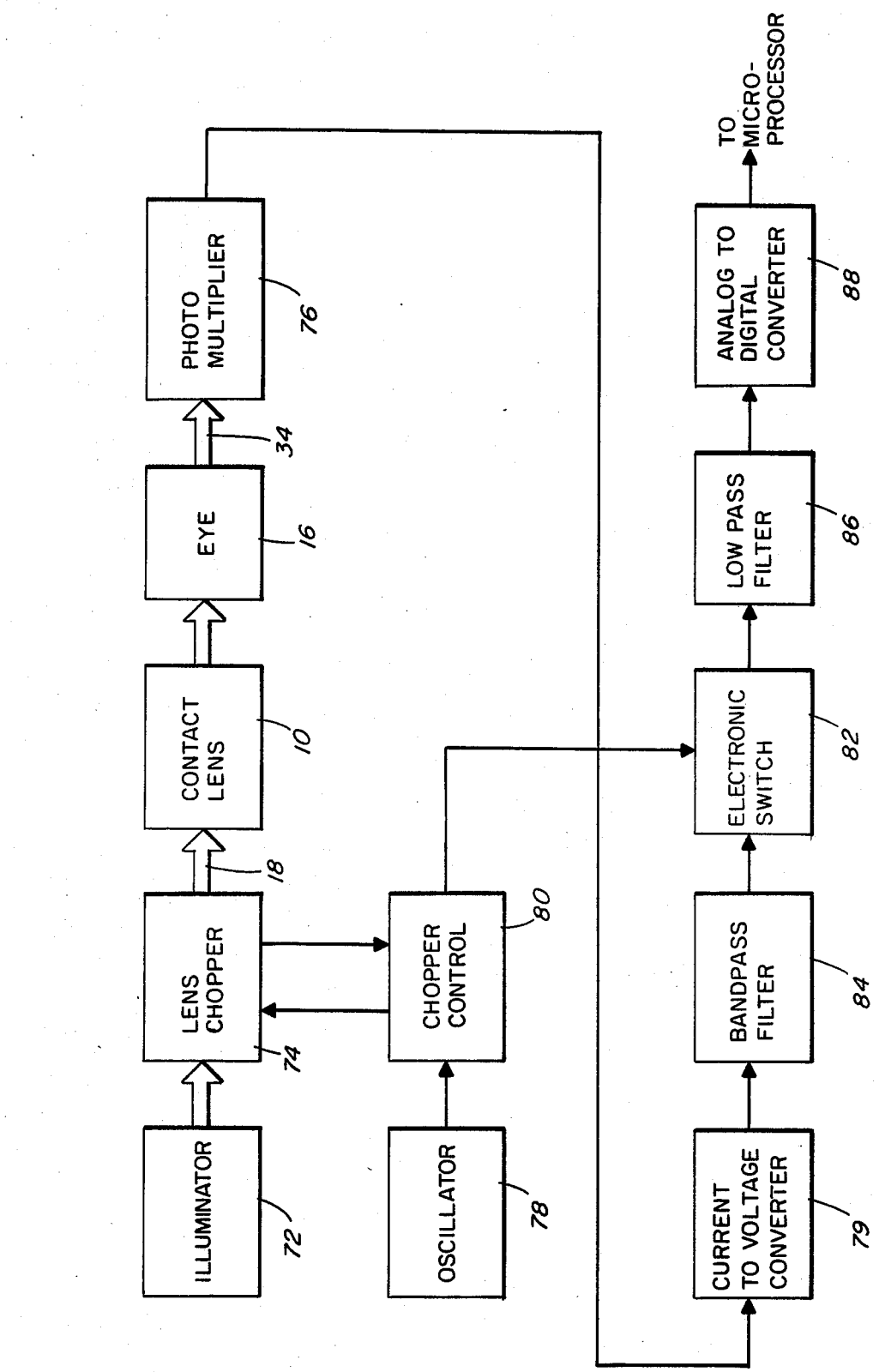
FIG. 5 is a block diagram of the system including associated electronic circuitry.

A block diagram of an overall system including the electronic circuitry which may be used with either of the embodiments of FIGS. 1 and 4 is presented in FIG. 5. Since the fluorescent signal is weak and can vary over a hundred to one range, a low noise system was required to assure good signal to noise ratio at the lower end of this range. To that end, a synchronous detection approach is utilized. Specifically, a beam of light from an illuminator 72 is modulated by a rotating light chopper 74 to a frequency of 390 Hertz. The light is passed through the fiber optic bundle 18 to the contact lens assembly 10. Fluorescent light from the eye 16 is sensed either directly by a photodiode or through a bundle 34 by a photomultiplier 76 or a photodiode. Electrical output from the photomultiplier 76 is applied to an analog amplifier in the form of current to voltage converter 79. The peak to peak value of the voltage output is related to the dye concentration in the anterior chamber. The signal and associated electrical noise are applied to a bandpass filter 84.

The frequency of modulation of the light passing through the light chopper is determined by an oscillator 78 through a chopper control circuit 80. The circuit 80 also applies a signal to an electronic analog switch 82 which provides synchronous detection. The bandpass filter 84 passes only signals at the 390 Hertz frequency set by the chopper 74. The analog switch 82 multiplies the filtered signal by a 390 Hertz signal from the chopper control 80 so as to generate a zero frequency (D.C.) signal and a 780 Hertz signal at the output of the switch.

The output of the switch 82 is applied to a low pass filter 86 to extract the D.C. signal, and to reject noise which is not phase-locked to the chopper frequency. The low pass filter output is applied to an analog to digital converter 88. The analog to digital converter 88 supplies a digital signal indicative of the anterior chamber fluorescing dye concentration to a microprocessor for further processing.

While the invention has been particularly shown and described with references to a preferred embodiment thereof, it will be understood by those skilled in the art that various changes in form and details may be made therein withoutdeparting from the spirit and scope of the invention as defined by the appended claims.

I claim:

1. A device suitable for detecting the fluorescence of the aqueous humor in the anterior chamber of an eye comprising:
    a flexible water impermeable contact lens membrane for placement against the cornea of the eye;
    a fluid enclosed in a fluid chamber by the contact lens membrane;
    means for changing the pressure of the fluid in the chamber to change the curvature of the flexible contact lens membrane;
    a light source;
    a mirror mounted to one side of the contact lens membrane for reflecting light from the light source through the contact lens membrane across the anterior chamber of the eye; and
    means for detecting light which passes outwardly from the anterior chamber through the contact lens membrane and the fluid chamber.

2. A device as claimed in claim 1 wherein the means for changing the pressure of the fluid is a syringe.

3. A device as claimed in claim 1 wherein the light directed across the anterior chamber is a ribbon of light.

4. A device as claimed in claim 1 wherein the light source is a fiber optic bundle.

5. A device as claimed in claim 1 wherein thwe means for detecting light comprises a fiber optic bundle.

6. A device as claimed in claim 1 wherein the flexible contact lens membrane is a membrane of polyvinyl chloride.

7. A device as claimed in claim 1 wherein the flexible contact lens membrane is fixed about its periphery to a barrel which forms the fluid chamber.

8. A device as claimed in claim 1 further comprising a flexible light stop which presses against the contact lens membrane throughout a range of curvatures.

9. A contact lens to be positioned against eyes having a range of curvatures comprising:
    a flexible contact lens membrane for placement against the cornea of the eye;
    a fluid enclosed in a fluid chamber by the contact lens membrane; and
    means for changing the pressure of the fluid in the chamber to change the curvature of the flexible contact lens membrane.

10. A contact lens as claimed in claim 9 wherein the means for changing the pressure is a syringe.

11. A method of detecting fluorescence of the anterior chamber of the eye comprising:
    providing fluorescent material in the anterior chamber of the eye:
    by means of a mirror mounted to a contact lens, projcting a beam of light from the side of the eye across the anterior chamber in a direction about perpendicular to the optic axis of the eye such that the light does not illuminate the lens of the eye; and
    detecting, from the front of the eye, fluorescent light from the anterior chamber.

12. A method as claimed in claim 11 wherein the light is projected as a ribbon of light across the anterior chamber.

13. A method of detecting fluorescence of the anterior chamber of the eye comprising:

providing fluorescent material in the anterior chamber of the eye;

positioning a contact lens against the cornea of the eye;

projecting a beam of light from the side of the eye through the contact lens across the anterior chamber in a direction generally perpendicular to the optic axis of the eye such that the light does not illuminate the lens of the eye; and detecting fluorescent light from the anterior chamber.

14. A method as claimed in claim 13 wherein the light is projected as a ribbon of light across the anterior chamber.

* * * * *